US011596574B2

(12) United States Patent
Pahl et al.

(10) Patent No.: US 11,596,574 B2
(45) Date of Patent: Mar. 7, 2023

(54) MASSAGE DEVICE FOR PRESSURE WAVE MASSAGE

(71) Applicant: FUN FACTORY GMBH, Bremen (DE)

(72) Inventors: Michael Pahl, Delmenhorst (DE); Dirk Bauer, Bremen (DE)

(73) Assignee: FUN FACTORY GMBH, Bremen (DE)

( * ) Notice: Subject to any disclaimer, the term of this patent is extended or adjusted under 35 U.S.C. 154(b) by 463 days.

(21) Appl. No.: 16/628,588

(22) PCT Filed: Jul. 3, 2018

(86) PCT No.: PCT/EP2018/068001
§ 371 (c)(1),
(2) Date: Jan. 3, 2020

(87) PCT Pub. No.: WO2019/007988
PCT Pub. Date: Jan. 10, 2019

(65) Prior Publication Data
US 2020/0214932 A1 Jul. 9, 2020

(30) Foreign Application Priority Data

Jul. 5, 2017 (DE) ..................... 20 2017 104 021.6

(51) Int. Cl.
*A61H 23/02* (2006.01)
*A61B 10/00* (2006.01)
*A61H 19/00* (2006.01)

(52) U.S. Cl.
CPC ..... *A61H 23/0236* (2013.01); *A61B 10/0045* (2013.01); *A61H 19/34* (2013.01);
(Continued)

(58) Field of Classification Search
CPC .. A61H 23/02; A61H 23/0218; A61H 9/0007; A61H 9/005; A61H 9/0057;
(Continued)

(56) References Cited

U.S. PATENT DOCUMENTS

| 5,377,701 A | 1/1995 | Fang |
| 6,099,463 A | 8/2000 | Hockhalter |

(Continued)

FOREIGN PATENT DOCUMENTS

| DE | 20 2009 008 634 U1 | 10/2009 |
| DE | 10 2013 110 501 A1 | 3/2015 |

(Continued)

OTHER PUBLICATIONS

Adam M., "Test du Womanizer W500, le meilleur sextoy du monde!", retrieved from https://www.nouveauxplaisirs.fr/test-du-womanizer-w500/17242, published Oct. 15, 2015, 30 pages.
(Continued)

*Primary Examiner* — Margaret M Luarca
*Assistant Examiner* — Cana A Gallegos
(74) *Attorney, Agent, or Firm* — Seed IP Law Group LLP

(57) ABSTRACT

A massage device for massaging by means of pressure waves includes a housing having a handle segment and a massage segment and at least one chamber comprising an opening leading outward in the massage segment. The chamber includes an end wall segment, a first circumferential wall segment, and a second circumferential wall segment, the first circumferential wall segment being disposed between the end wall segment and the second circumferential wall segment, and the second circumferential wall segment defining the opening with the end wall segment being at least partially displaceable. The massage device further includes a drive device for inducing a predetermined vibration in the end wall segment, with the first circumfer-
(Continued)

ential wall segment being substantially rigid and the second circumferential wall segment being substantially flexible.

25 Claims, 7 Drawing Sheets

(52) U.S. Cl.
CPC .. *A61H 23/0218* (2013.01); *A61B 2010/0074* (2013.01); *A61H 2201/0153* (2013.01); *A61H 2201/5058* (2013.01); *A61H 2201/5064* (2013.01); *A61H 2201/5092* (2013.01)

(58) Field of Classification Search
CPC .... A61H 19/34; A61H 19/30; A61H 23/0227; A61H 23/0236; A61H 19/43
See application file for complete search history.

(56) References Cited

U.S. PATENT DOCUMENTS

| | | | |
|---|---|---|---|
| 6,464,653 | B1 | 10/2002 | Hovland |
| 2012/0089056 | A1* | 4/2012 | Jiang .................... A61F 13/84 601/46 |
| 2013/0012769 | A1 | 1/2013 | Carlson |
| 2014/0336548 | A1* | 11/2014 | Lee .................... A61H 23/0263 601/48 |
| 2016/0022533 | A1* | 1/2016 | Makower ............... A61H 23/00 601/46 |
| 2016/0213557 | A1* | 7/2016 | Lenke ................ A61H 23/0263 |
| 2018/0125748 | A1* | 5/2018 | Goldenberg ....... A61H 23/0263 |

FOREIGN PATENT DOCUMENTS

| | | | |
|---|---|---|---|
| EP | 3 228 297 | A1 | 10/2017 |
| GB | 819615 | A * | 9/1959 |
| KR | 20110131338 | A * | 12/2011 |
| RU | 2 343 896 | C2 | 4/2006 |
| RU | 92 615 | U1 | 3/2010 |
| WO | 2006/058291 | A2 | 6/2006 |
| WO | 2008/028076 | A2 | 3/2008 |
| WO | 2015/039787 | A1 | 3/2015 |
| WO | 2017/158107 | A1 | 9/2017 |

OTHER PUBLICATIONS

"Lovehoney Humdinger Klitoris-Vibrator", www.lovehoney.de/product.cfm?p=21149, Wayback Machine retrieval from Mar. 13, 2017, 1 page.

Screenshot from https://d3f650ayx9w00n.cloudfront.net/940/52411.jpg, Wayback Machine retrieval from Apr. 17, 2017.

"Womanizer W100 USB aufladbarer Klitoris-Stimulator", www.lovehoney.de30/product.cfm?p=32547, Wayback Machine retrieval from Nov. 5, 2015, 1 page.

* cited by examiner

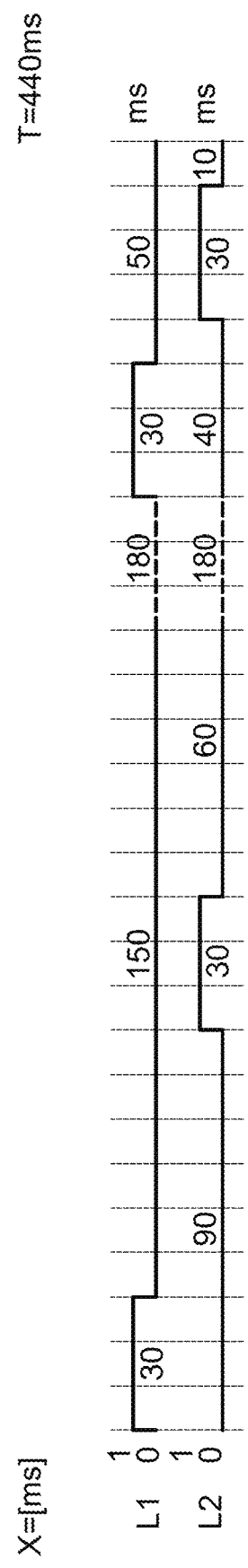
FIG. 8A
FIG. 8B

MASSAGE DEVICE FOR PRESSURE WAVE MASSAGE

BACKGROUND

Technical Field

The disclosure relates to a massage device for massaging by means of pressure waves, comprising a housing having a handle segment and a massage segment.

Description of the Related Art

Conventional vacuum devices are used for indirectly stimulating erogenous zones and particularly the clitoris in order to stimulate the erogenous zones of the affected person without directly contacting the main area to be stimulated. For example, vacuum pumps for the female primary or secondary sexual organs are known, typically comprising a suction cup for placing and a hand pump. The vacuum applied to the clitoris, for example, by means of such a device generates a negative pressure in the clitoris itself, typically lower than the systolic blood pressure. Said pressure differential leads to expansion of the clitoris and/or stimulates blood flow into the affected region. Said clitoral vascular engorgement both promotes arousal by increasing sensitivity and facilitates optical and haptic manipulation. The improved blood flow also leads to increased discharge of vaginal moisture, making the stimulation more pleasant. Manual actuation of the hand pump, however, is often difficult or distracting. Said category of devices can also lead to habituation effects from the long-term, uninterrupted use of vacuum, limiting the long-term effectiveness of the device. Simply increasing blood flow in the clitoris is also often insufficient for reaching climax, so that vacuum pumps are often used only as foreplay in order to achieve climax through subsequent direct (pressure) massage of the erogenous zones.

Instead of a manually operated vacuum pump, electrically powered vacuum pump are increasingly used. As an example, WO 2006/058291 A2 discloses a device for sexual therapy wherein the arrangement comprises a tube-shaped suction chamber for the clitoris, an electric vacuum source (vacuum pump), and a plurality of airflow openings. The suctioned moist air leads to contamination of the fluidically downstream vacuum arrangement, such as the vacuum pump. Such arrangements having vacuum pumps can be problematic in terms of hygiene, because vacuum pumps and the associated valves and airflow components often comprise dead spaces or corners and/or are difficult to clean. The device is further used for therapy of the blood vessels of the clitoris, and not for stimulation to sexual climax.

U.S. Pat. No. 6,099,463 A discloses a device for stimulating the clitoris by means of a tube-shaped suction chamber, a vacuum source or vacuum pump, and a plurality of valves by means of which the magnitude of the vacuum is controlled. The vacuum can thereby also be used in a cyclic form in order to achieve the stimulation effect, wherein habituation effects are also to be expected due to the use of a continuous vacuum. The disadvantages described above of hygiene and drying out of the skin area to be stimulated are present again here. The pressure system arrangement having a plurality of valves, vacuum pumps, etc., is also relatively complex.

U.S. Pat. No. 6,464,653 B1 discloses therapeutic devices and methods for generating clitoral engorgement by means of a vacuum produced by means of a vacuum pump in order to support treatment of dysfunction of the clitoris. The level of vacuum in the suction chamber is manually adjusted or varied by means of a control valve or modulator to be covered accordingly by a finger. This requires the attention of the user and can sometimes be distracting or disturbing. Said relatively complex device having further valves also has the disadvantages of hygiene and drying out as described above, wherein the device also serves for long-term therapeutic purposes and not short-term sexual stimulation.

WO 2008/028076 A2 discloses a therapeutic device for women serving primarily for treating sexual dysfunction. The device thereby comprises a combination of indirect stimulation by means of a vacuum chamber and direct stimulation by means of mechanical vibrators and oscillators.

For said therapeutic device, the vacuum serves for increasing blood flow in the clitoris, while the actual stimulation or massage of the skin area is done by means of direct mechanical vibrations or oscillations. A suction cup for placing on the skin area to be stimulated is connected internally to a motor by means of a mechanical connection. The suction cup is expanded by the motor after the device is activated, wherein the volume of the suction cup expands. The resulting volume of the suction cup and thus the strength of the vacuum can be adjusted by means of control elements on the device. The air displaced by the suction process in the device is discharged outward by means of a tube. The vacuum in said device has only a supporting function, while the actual stimulation is done directly, causing the disadvantages of direction stimulation described above.

US 2013/0012769 A1 discloses a device wherein a pulsating high pressure is used for stimulating as an air-pressure massage. A pump or a compressor generates a pulsating high pressure directed by means of a nozzle toward the erogenous zone to be stimulated. For said device, the affected skin area dries out very severely. A temperature difference is also typically present between the temperature of the infed air and the temperature of the skin area to be stimulated and can sometimes be perceived as disturbing. The problems of hygiene described above also arise for said device, wherein in this case pathogens or germs or other contaminants potentially present in the device can also be transported directly to the genital area of the user.

The devices of the prior art thus have the disadvantage in common that the complexity of arrangements for producing vacuum or high pressure is high, and that said device can have hygienic problems.

One such massage device is fundamentally known from WO 2015/039787 A1. The stimulation device for erogenous zones, particularly for the clitoris, disclosed therein comprises a pressure field generating device having at least one first chamber and at least one second chamber having at least one opening for placing on a body part, and at least one connecting element connecting the first chamber to the second chamber, and a drive unit modifying the volume of the first chamber such that a stimulating pressure field is generated in the second chamber by means of the connecting element, and a control device for actuating the drive unit. The drive unit is implemented as an electric motor and drives the first chamber via an axle by means of an eccentric shaft or by means of a piston rod, such that the volume of the first chamber is modified according to the rotation of the axle of the drive unit.

The relatively complex structure thereof is disadvantageous, as is the limited displacement opportunity and thus limited ability to generate vibrations.

BRIEF SUMMARY

The object of the present disclosure is to disclose such a massage device having simpler construction and nevertheless able to generate a greater variety of different vibrations.

The object is achieved by a massage device for massaging by means of pressure waves according to a first consideration of the disclosure and having the features of claim 1. The massage device according to the disclosure comprises at least one chamber comprising an opening leading outward in the massage segment, the chamber comprising an end wall segment, a first circumferential wall segment, and a second circumferential wall segment, the first circumferential wall segment being disposed between the end wall segment and the second circumferential wall segment, and the second circumferential wall segment defining the opening, the end wall segment being at least partially displaceable and the massage device comprising a drive device for inducing a predetermined vibration in the end wall segment, and wherein the first circumferential wall segment is substantially rigid and the second circumferential wall segment is substantially flexible. The predetermined vibration preferably corresponds to a specified vibration profile. While massage devices according to the prior art typically comprise two chambers, namely one chamber, the volume of which is modified in order to then generate a pressure field in a second chamber via a connection, a first embodiment of the massage device according to the present disclosure comprises only one single chamber open to the outside. Therefore, no flow occurs between two chambers, whereby cleaning is substantially simplified. The chamber is preferably substantially free of undercuts. Cleaning is thereby further facilitated. The second circumferential wall segment is substantially flexible and defines the opening. A pleasant contact surface is thereby achieved. Because the first circumferential wall segment is substantially rigid, dimensional stability is provided and cleaning is further facilitated. The end wall segment is displaceable and can be implemented as a membrane overall, for example. The end wall segment is preferably disposed opposite the opening. A particularly pleasant massage can thereby be achieved, because the end wall segment can be displaced toward the opening and thus a longitudinal wave can be generated. In other embodiments, it is also conceivable that the end wall segment is slightly laterally offset, whereby an ergonomic structure may be able to be achieved. Besides the opening leading outward, the chamber comprises no further openings. That is, the opening leading outward is the only opening of the chamber. It should be understood that there can also be embodiments of the disclosure comprising only one circumferential wall segment and particularly no first circumferential wall segment. For such embodiments, the entire wall bounding the chamber is preferably flexible. There can also be embodiments also having a second chamber adjacent to the first.

It is preferable that the first and the second circumferential wall segment have approximately the same diameter. It is fundamentally conceivable that the circumferential wall segments have any contour, particularly such as circular, polygonal, such as hexagonal or octagonal, oval, star-shaped, or the like. A substantially circular shape, however, also further facilitates cleaning. For example, a user of the massage device can penetrate into the chamber with a rag or a brush in order to clean said chamber from the inside. It is thereby preferable that the chamber comprises as few protrusions, recesses, bends, and the like.

It can also be provided that the chamber has a substantially cylindrical or conical shape tapering down in the direction of the end wall segment. A conical shape can also be cleaned particularly well. The chamber preferably comprises no undercuts, starting from the opening, in which fluid could collect.

According to a preferred refinement, the first circumferential wall segment is made of a hard plastic material and is optionally radially coated on the inside. The hard plastic can particularly be PE or PVC, PEEK, or the like. The first circumferential wall segment therefore provides stability for the chamber, while the second circumferential wall segment provides a pleasant contact and certain amount of adaptation of the opening to the bodily anatomy at which the massage device is to be used. It is indeed fundamentally possible to use the massage device so that the opening and the second circumferential wall segment do not make contact with a body part, but particularly effective massage is achieved if the opening is closed by contact with a body part. Genital organs can particularly be massaged in this manner. It is conceivable that the chamber is coated on the inside, for example having a silicone coating or the like. It can also be provided that only the first circumferential wall segment has a coating.

The second circumferential wall segment is preferably formed of a silicone material. Other materials, such as TPE, are fundamentally also conceivable, but silicone material has been found to be particularly suitable for skin contact. Silicone is perceived as pleasant and is largely accepted.

The silicone material is particularly preferably a medical silicone material having a Shore hardness in a range from Shore 5 to Shore 50, preferably Shore 5 to Shore 30, further preferably Shore 10 to Shore 20. A value of approximately Shore 15 is particularly preferred. The Shore values are each measured as Shore A values. Silicone material having a Shore value in said range is perceived as particularly pleasant and is particularly suitable for massaging body parts. It is thereby further preferable that the second circumferential wall segment has a wall thickness in a range from 0.5 mm to 5 mm, preferably 1 mm to 4 mm, further preferably 1 mm to 3 mm, particularly preferably 1 mm to 2 mm. A wall thickness of approximately 1.5 mm is also particularly preferred. Particularly high flexibility of the second circumferential wall segment is thereby achieved, as well as a certain adaptability to the anatomy. It is preferable that not only the material of the second circumferential wall segment is flexible, but also the overall structure thereof, in order to achieve adaptability to the anatomy. Because the second circumferential wall segment has such a low wall thickness, the opening can also be stretched, and the second circumferential wall segment can be easily deformed overall, particularly by bringing the second circumferential wall segment into contact with a body part.

The second circumferential wall segment is preferably connected to the first circumferential wall segment by means of two-component injection molding. The first and the second circumferential wall segment can be formed as a single part and are thus directly connected to each other, and no gap is provided between the two components. Overall hygiene is thereby further improved.

In a further particularly preferred embodiment, the second circumferential wall segment is formed by a removable cap for connecting or connected to the first circumferential wall segment and/or the housing by means of a clamping connection. The removable cap can comprise a pass-through opening or can be closed, so that the cap then defines a second chamber, wherein the first chamber is formed between the end wall segment, the first circumferential wall segment, and the cap. In this case, the second chamber forms the opening. The two chambers are not connected in this case. It can be provided that an incompressible fluid is provided in the first, closed chamber in order to transmit displacements from the end wall segment to the cap with little damping. It is preferable, however, that the cap comprises a pass-through opening, so that the chamber is a single overall piece and is formed by the end wall segment, the first circumferential wall segment, and the second circumferential wall segment of the cap. The second circumferential wall segment is preferably reversibly and non-destructively removable and replaceable for cleaning purposes, particularly without tools. Operation is thereby particularly facilitating and a user can remove the second circumferential wall segment. It is also possible to replace the second circumferential wall segment if said segment is damaged, or to replace said segment with various sizes, shapes, or materials in order to adapt the massage to personal needs.

The second circumferential wall segment is preferably connected to the first circumferential wall segment and/or to the housing in a clamping manner. To this end, the second circumferential wall segment preferably bears on a radially outward segment of the first circumferential wall segment or housing. That is, the second circumferential wall segment partially radially outwardly covers the first circumferential wall segment, but does not extend into the interior thereof. Hygiene is also thereby improved. If the second circumferential wall segment is flexible and particularly formed of a silicone material, then said segment can be received at an outer circumferential segment of the first circumferential wall segment or of the housing in a clamping manner by expanding slightly.

To this end, it is preferably provided that an annular bulge for engaging behind is implemented on the first circumferential wall segment and/or the housing and bounds a radially outwardly open circumferential groove, and the second circumferential wall segment comprises a corresponding radial protrusion for engaging in the circumferential groove in order to attach the second circumferential wall segment to the first circumferential wall segment or the housing by clamping. The annular bulge engaging in the circumferential groove also achieves axial fixing of the second circumferential wall segment or the cap. Said cap can be pulled off of the housing only by overcoming the elastic deformation when the annular bulge slides out of the circumferential groove.

It is further preferable if an axially open annular groove is implemented on the first circumferential wall segment and/or the housing, and the second circumferential wall segment comprises a corresponding axial protrusion for engaging in the annular groove in order to produce a sealing closure. Even better fit is thereby achieved. The axial annular groove also preferably serves for preventing radial spreading of the second circumferential wall segment, so that the fit of the second circumferential wall segment on the first circumferential wall segment or the housing is improved.

According to a further preferred embodiment, the second circumferential wall segment comprises an inner collar extending radially and integrally formed on the second circumferential wall segment spaced apart from the opening. At least partial closure can thereby be provided between a region defined by the first circumferential wall segment and a second region defined by the first circumferential wall segment.

According to a further preferred embodiment, the drive device comprises at least one coil element and at least one magnetic core displaceably guided and disposed parallel to the coil element and connected to the end wall segment.

If an electrical current is applied to a coil element, a magnetic field forms and interacts with the magnetic core such that said core is displaced in parallel, preferably coaxially, to the center axis of the coil element. By applying electrical current to the coil element accordingly, a back-and-forth motion of the magnetic core can thus be induced. The back-and-forth motion, that is, a vibration, can thereby be influenced in both frequency and amplitude by exciting the coil element accordingly. A wide variety of vibrations can thus be generated, wherein the effect of the magnetic core on the end wall segment produces a pressure field in the first chamber superimposed on an ambient pressure. The fluid (air or water) present in the chamber is induced to vibrate, and said vibration can be perceived by the body part being excited, stimulated, or massaged by the vibrating fluid. Pressure waves thus form and the emitted pressure waves can be used advantageously for massaging particular body parts.

The coil element preferably comprises two coils actuated alternately in order to displace the magnetic core. It is also alternatively possible that the coil element comprises only one coil for actuating in a bipolar manner in order to displace the magnetic core accordingly in opposite directions.

Such a pressure field is a field of media pressures changing over time, for example, comprising temporary high pressures and low pressures, wherein a low pressure is a media pressure below the reference pressure, and a high pressure is a media pressure above the reference pressure.

Overall, the implementation of the drive device having the coil element and the magnetic core achieves particularly quiet driving. The magnetic core is displaced back and forth in the coil element and transmits the motion to the end wall segment implementing the pressure field in the chamber. This means that only very few moving elements are provided in the drive device, and the magnetic core particularly does not make contact with the coil element. It can be provided that a tube or the like in which the magnet core slides is first provided in the coil element. The tube is then preferably formed of a friction-reducing material, such as a plastic or a cardboard material.

Rotating motors are provided in the prior art, using a piston rod drive and typically an intermediate gearbox for transforming the rotational motion thereof into a back-and-forth motion of a chamber wall. Both have relatively high noise production and are therefore disadvantageous.

The magnetic core is preferably fixedly and directly connected to the end wall segment. For example, the magnetic core is glued directly to the end wall segment. The end wall segment is preferably implemented as a thin membrane made of a plastic or silicone material. It can also be provided that an annular protrusion is provided on the end wall segment, in which the magnetic core is partially embedded. It can also be provided that the magnetic core is fixedly clamped by means of particular clamping means to protrusions provided to this end on the end wall segment.

The direction of motion of the magnetic core is preferably substantially perpendicular to the end wall segment, that is, to a plane defined by the end wall segment. The chamber preferably comprises a center axis corresponding to the axis of rotation if the chamber is cylindrical in shape. The magnetic core is preferably displaced along the center axis or offset parallel to the same. The stroke of the magnetic core is thereby transmitted to a maximum of one motion of the end wall segment, and a maximum stroke of the end wall segment can be executed. Effective pressure wave formation is thereby possible.

According to a preferred embodiment, the magnetic core is connected to the end wall segment by means of a screw connection. To this end, the massage device comprises a screw extending through the end wall segment and a central through hole in the magnetic core and received in a nut. It can be provided that the screw head of the screw is disposed within the chamber and contacts the interior of the chamber at the end wall segment. It can also be provided that the screw head is covered by a coating after assembly in order to make said screw head not visible. The magnetic core is preferably clamped between the end wall segment and the nut by means of the screw.

The massage device preferably comprises a guide element for guiding the magnetic core relative to the coil element. The magnetic core is guided by means of the guide element, particularly coaxially to the coil element. The guide element preferably slides in a corresponding receptacle on the housing, or in a receptacle fixedly connected to the housing. The guide is preferably implemented as a sliding guide. Particularly little noise is generated thereby.

The nut particularly preferably forms the guide element. In this case, the nut is preferably implemented as an elongated bushing comprising an internal thread. Alternatively, the nut is implemented as a plastic sleeve and the thread is cut by threading in the screw during assembly. The plastic sleeve in this case preferably has an axial length allowing guiding of the same on a corresponding counter guide, particularly such as a cover having a through hole, disposed on the coil element, or the coil element itself.

According to a further preferred embodiment, the massage device comprises a control unit for controlling the drive device. The control unit controls the drive device such that the predetermined vibration is induced in the magnetic core. The control unit preferably comprises a storage unit having a plurality of pre-stored, specified vibration profiles. An energy source in the form of a rechargeable battery is further provided, by means of which electrical current is provided to the coil element. The control unit is preferably coupled to at least one control knob on the handle segment of the massage device. At least two, three, or four control knobs are provided. One control knob is provided, for example, for switching the massage device on or off, and a second control knob is used to select a predefined vibration from the plurality of saved, specified vibration profiles. A second and third control knob are alternatively provided, wherein an intensity of the vibration, for example measured using the amplitude, can be increased by means of the second, and can be decreased by means of the third.

The massage device further preferably comprises a measuring unit for determining a location of the magnetic core relative to the coil element and for providing the determined location to the control unit, wherein the control unit is set up for controlling the drive unit as a function of the determined location. A control is thereby implemented and the drive device can be electrically actuated by means of active control.

The measuring device can comprise an optical sensor in a first variant for optically measuring a position of the magnetic core. It is also alternatively possible to determine the location of the end wall segment. Said determining can also be done optically by means of an optical sensor.

In a further variant, the measuring device comprises a Hall-effect sensor for capturing the magnetic field of the magnetic core. The Hall-effect sensor is preferably stationary and thus captures the change in the magnet field as the magnetic core is displaced. For example, such actuating of the drive device is possible, as a function of a pressing force at which the massage device is pressed against a body part. For example, when using the massage device under water and when pressing firmly against the body, the vibration of the end wall segment can be damped more severely than in an air atmosphere when pressing lightly. This can be compensated for when implementing the control circuit, as the position of the magnetic core is captured. If it is determined that the stroke actually executed by the magnetic core does not correspond to the stroke to be achieved according to the predetermined vibration profile, then the control unit is preferably implemented for modifying the actuating of the drive device such that the stroke of the magnetic core corresponds to the predetermined stroke. It is thereby achieved that a user experiences a corresponding massage, regardless of the type of operation of the massage device, when selecting a corresponding vibration profile, largely regardless of the medium in which the massage device is used.

The disclosure further proposes a massage device, preferably a massage device according to any one of the preceding claims, wherein a noise emission does not exceed 40 dBA when the drive device is activated. The noise emission preferably does not exceed 38 dBA, 37 dBA, or 35 dBA. Said noise emission is measured at room temperature of 25° C., standard pressure, and air atmosphere by means of the measuring device: PCE-322A Data Logger Sound Level Meter from PCE Instruments Ltd., Southampton, United Kingdom. The measuring device is set up at a distance of 30 cm from the opening, wherein the massage device is clamped at the handle segment and free at the massage segment. The measuring device and the massage device were set up by means of a stand placed in a room having a wood floor. In a test measurement, the base sound pressure level was 36 dBA.

It is further preferable that 80% or more of the emitted sound lies in a frequency range from 40 to 200 Hz, preferably 60 to 120 Hz. No more than 50% of the spectrum preferably lies above 200 Hz, preferably at 300 Hz or greater. No more than 40%, no more than 30%, no more than 20%, no more than 10% is preferably above 200 Hz, preferably at 300 Hz. No more than 10% of the spectrum preferably lies above 400 Hz, 500 Hz, 600 Hz, 700 Hz, or 1000 Hz.

Preferably 80% or more of the emitted sound is pink noise ($1/f$ noise) or red noise ($1/f^2$ noise). It has been found that a particularly pleasant feeling is thereby achieved for the massage. Both a low noise emission level and a noise emission level in the range of pink or red noise lead to a relaxed, pleasant massage feeling, acoustically amplified. A "rich" sound is emitted, not high squeaking or the like. When massaging body parts, particularly for stimulating massage of genitals, not only the purely physical massage is important, but rather the acoustic perception of the user as well. If a pleasant sound is emitted, then the relaxation effect is significantly greater than if a more mechanical sound is emitted. Because noise emission can never be fully prevented for moving parts, the inventors of the present disclosure have found that a sound level of 40 dBA or lower, but preferably not less than 30 dBA when simultaneously emitting in the range of pink noise or red noise is perceived as particularly pleasant. If a frequency range of 60 to 120 Hz is reached simultaneously, that is, a pleasant, sonorous hum, then the user immediately has a comforting feeling, whereby the actual physical massage effects are substantially enhanced.

The disclosure further proposes a massage device wherein a predetermined vibration is a non-sinusoidal vibration. Such a non-sinusoidal vibration can be particularly a sawtooth vibration, a rectangular vibration, a triangular vibration, or a mixture thereof. This is made possible particularly by driving by means of the magnetic core and the coil element. The predetermined vibration preferably has a variable amplitude. A particularly pleasant massage is thereby achieved. It is possible, for example, to provide a vibration wherein every tenth amplitude is increased. A variable-amplitude vibration can also be a sinusoidal vibration. It can also be provided that the sinusoidal vibration is superimposed on a second sinusoidal vibration and thus represents an envelope vibration. In this case, the amplitude varies continuously, or the vibration can be implemented as a type of wobble signal.

Finally, the disclosure proposes a method for removing a sample of vaginal fluid, having the steps: placing the opening of a massage device according to any one of the embodiments of a massage device described above on a female clitoris, actuating the massage device, collecting vaginal fluid in the chamber, and removing the massage device. The extracting of a sample of vaginal fluid is thereby substantially facilitated and made more pleasant for the patient. The method preferably also comprises taking a sample smear from the chamber by means of a swab. The method preferably comprises the step of changing out the second circumferential wall segment after extracting the sample. The second circumferential wall segment can, together with the sample of vaginal fluid, be removed and sent to a laboratory, for example. During operation, the massage device stimulates the flow of vaginal fluid, so that extracting the sample is substantially facilitated.

BRIEF DESCRIPTION OF THE SEVERAL VIEWS OF THE DRAWINGS

The disclosure is described in more detail below, using two embodiment examples and referencing the attached figures. Shown are:

FIGS. 8A-8B are impulse diagrams for actuating a coil element of embodiments according to the present disclosure.

DETAILED DESCRIPTION

Figure 1:
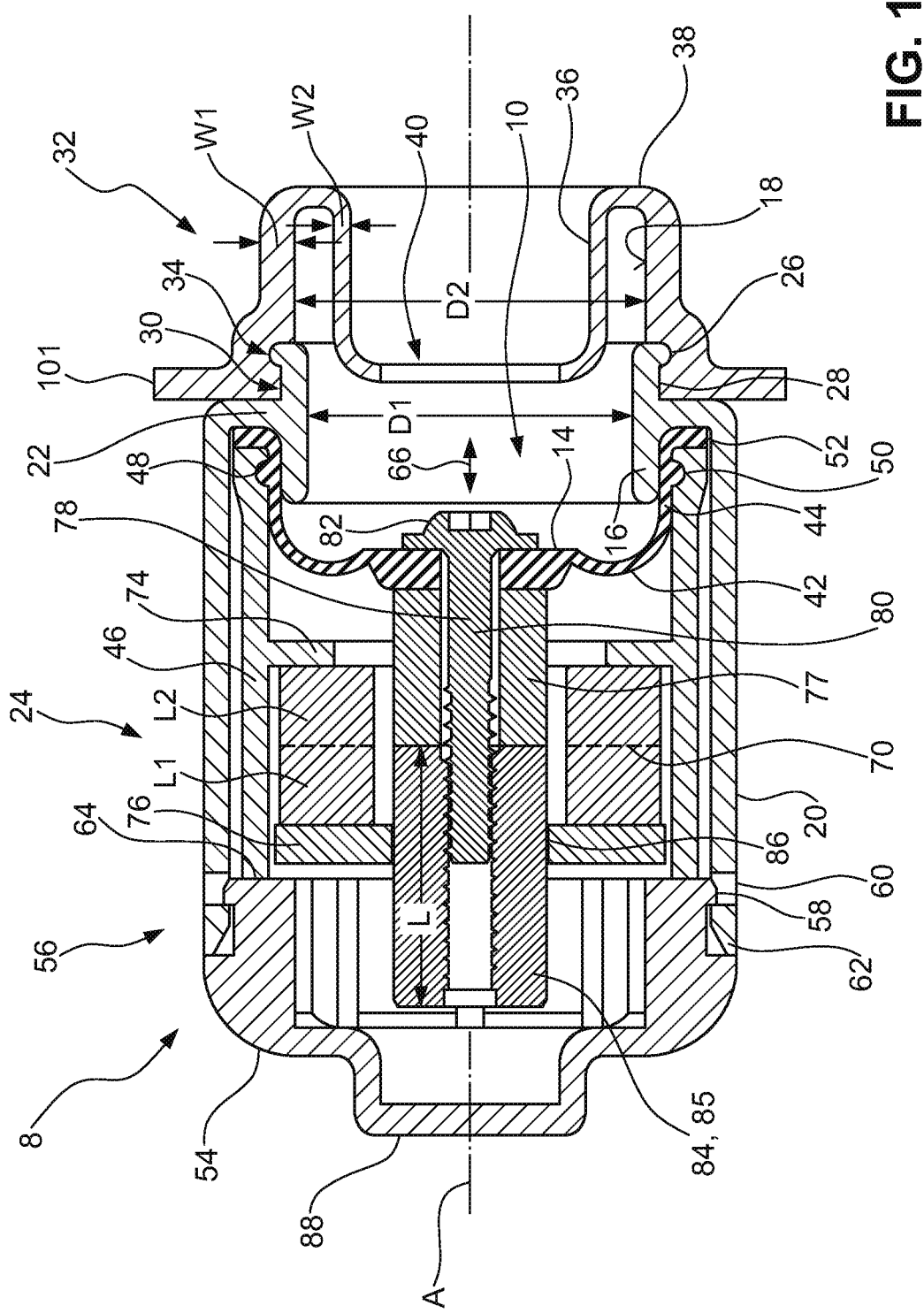
FIG. 1 is a full cross section through a massage unit of a massage device.

A massage device 1 (FIG. 2) comprises a housing 2 having a handle segment 4 and a massage segment 6. A massage unit 8, described in more detail below, is disposed in the massage segment 6. The massage unit 8 concretely serves for the massage and is inserted in the housing 2. The housing 2 can comprise any various shape. The housing is substantially shown as a handheld device is FIG. 2, but the housing 2 can also be rod-shaped overall and can be very closely nestled against the massage unit 8. Other variants are also conceivable, particularly such as U-shaped configurations of the housing 2 or configurations wherein the massage unit 8 is pivotally disposed.

FIG. 1 shows a magnified view of the massage unit 8 by means of which individual elements of the massage unit 8 and thus also of the massage device 1 are described.

The massage unit 8 defines a chamber 10 having an opening 12 leading outward. The chamber 10 comprises an end wall segment 14, a first circumferential wall segment 16, and a second circumferential wall segment 18. The first circumferential wall segment 16 is disposed between the end wall segment 14 and the second circumferential wall segment 18. The opening 12 is formed by the second circumferential wall segment 18.

It should be understood that there can also be embodiments wherein no second circumferential wall segment 18 is provided. In such cases, the first circumferential wall segment 16 can be extended in the axial direction, that is, in the direction of the center axis A, so that the first circumferential wall segment 16 then defines the opening 12. The chamber 10 is substantially cylindrical in overall design, wherein the first circumferential wall segment 16 has a first diameter D1 and the second circumferential wall segment 18 has a diameter D2. As can be seen from FIG. 1, the second diameter D2 is somewhat greater than the first diameter D1. The end wall segment 14 is substantially flat and extends substantially perpendicular to the center axis A.

It should be understood, however, that there can also be other configurations of the chamber 10, particularly chambers comprising an oval configuration having a center axis A, or being conical, bell-shaped, hourglass-shaped, or the like. It can also be provided that a wall having a connecting element is provided between the first circumferential wall segment 16 and the second circumferential wall segment 18, for example implemented as a rigid channel or also as a flexible channel.

The first circumferential wall segment 16 is substantially rigid. The first circumferential wall segment 16 is made of a hard plastic, particularly PE, according to the present embodiment example (FIG. 1). In other embodiments, the first circumferential wall segment can also be made of a metal material and/or be implemented having an additional radial interior coating.

In the concrete embodiment example of FIG. 1, the first circumferential wall segment 16 is integrally connected to a housing 20 of the massage unit 8. The housing 20 of the massage unit 8 extends substantially cylindrically and is connected to the first circumferential wall segment 16 by means of a collar 22 extending radially. The housing 20 of the massage unit 8 also serves for supporting a drive device 24 provided inside the housing 20. The drive device 24 is described in detail below.

The end of the first circumferential wall segment 16 proximal to the opening 12 transitions into an annular bulge 26 for engaging behind, and said bulge then defines a circumferential groove 28 radially outwardly open between an outer circumferential surface of the first circumferential wall segment 16 and the collar 22. The second circumferential wall segment 18 is connected to the first circumferential wall segment 16, and in this case also to the housing 20, by means of said radially outwardly open circumferential groove 26. To this end, the second circumferential wall segment 18 comprises a corresponding radial protrusion 30 provided for engaging in the circumferential groove 28 in order to attach the second circumferential wall segment 18 to the first circumferential wall segment 16, and also in this case the housing 20, by clamping.

The second circumferential wall segment 18 is formed by a removable cap 32 in the present embodiment example (FIG. 1). The removable cap 32 is made entirely of a medical silicone material having a Shore A value of 15. Because the second circumferential wall segment 18 is entirely made of silicone material, said segment is flexible and can be radially expanded for assembling to the first circumferential wall segment 16, so that the protrusion 30 can slide over the annular bulge 26 in order to engage in the circumferential groove 28. In a similar manner, the first circumferential wall segment 18 comprises a radially inwardly open circumferential groove 34 in which the annular bulge 26 engages in the assembled state (FIG. 1).

According to the present particular embodiment example, the second circumferential wall segment 18 comprises a collar segment 36 extending back in the direction of the end wall segment 14 and extending back from an axial end 38 of the second circumferential wall segment 18. The collar segment 36 has a lesser wall thickness W2 than the second circumferential wall segment 18 having a wall thickness W1. The wall thickness W1 of the first circumferential wall segment 18 is approximately in the range of 1.5 mm, while the wall thickness W2 of the collar segment 36 extending back is approximately 0.5 mm. High flexibility of the second circumferential wall segment 18 and of the cap 32 is thereby achieved, because not only the material itself but also the overall structure is very flexible, so that the opening 12 is flexible and can be adapted in this manner to the anatomy by the user due to the low wall thickness W1, W2. Comfort is thereby substantially increased.

It should be understood that the inner collar 36 is not necessary, and that the second circumferential wall segment 18 can also end at the end 38. It is further possible that the collar segment 36 is not formed at the axial end 38, but rather extends exclusively radially and from a segment of the second circumferential wall segment 18 implemented adjacent to, particularly directly adjacent to, the groove 34.

It can also be seen in FIG. 1 that the collar 36 is open, that is, an aperture 40 is implemented in the second circumferential wall segment 18 so that fluid, for example, can penetrate through the opening 12 and come into direct contact with the end wall segment 14. An actual constriction of the diameter, however, is not provided overall.

The end wall segment 14 is implemented as a membrane 42 in the present embodiment example (FIG. 1). The membrane 42 is approximately cup-shaped overall and comprises a side wall 44 extending radially to outside of the first circumferential wall segment 16. In the present embodiment example, an assembly bushing 46 is provided for assembly and is approximately cylindrical and is disposed radially inside the housing 20. The assembly bushing 46 comprises an inner circumferential groove 48 in an end disposed proximally to the opening 12, in which a corresponding annular bulge 50 of the membrane 42 can engage. The membrane 42 further comprises a distal collar 52 enclosing the assembly bushing 46 at the end and pressed against the collar 22 of the housing 20 by an end face of the assembly bushing 46. The collar 52 of the membrane 42 is clamped in this respect between the assembly bushing 46 and the housing 20, particularly the collar 22 of the housing 20.

In order to sufficiently press the assembly bushing 46 against the collar 52, the assembly unit 8 comprises an end cap 54 connected to the housing 20 by means of a latching connection 56. Any other form-fit or and/or force-fit connection is also conceivable here. It can also be particularly provided that the end cap 54 is screwed against the housing 20. In the present embodiment example, however, the end cap 54 comprises one or more detent lugs 58 for latching into corresponding recesses in the housing 20, particularly through holes 60, from the inside. In order to facilitate assembly and particularly to deflect detent hooks on which the detent lugs 58 are attached, the housing 20 comprises an insertion bevel 62. The end cap 54 comprises an end face 64, an end face thereof distal to the opening 12 making contact with the assembly bushing 46 and thus pressing the assembly bushing 46 against the membrane 42, particularly the collar 52. Particularly good sealing between the membrane 42 and the first circumferential wall segment 16 is thereby achieved.

The membrane 42 is displaceable back and forth by means of the drive device 24, as indicated by the arrow 66. The volume of the chamber 10 is thereby reduced and the fluid present in the chamber 10 is induced to vibrate. A pressure field of pressure surges palpably provided at the opening 12 thus forms in the chamber 10. The principle is per se known and already described in the prior art.

The drive device 24 comprises a coil element 70 disposed coaxially about the center axis A for driving the membrane 42. The coil element 70 is connected to a control unit 72 (cf. FIG. 2) as described further below. The coil element 70 is retained between an assembly protrusion 74 and a guide washer 77. The assembly protrusion 74 is formed integrally on the assembly bushing 46, but can also be disposed separately therefrom and/or on the housing 20. The coil element 70 can be attached to the protrusion 74 by means of suitable attaching means, particularly such as an adhesive connection, a clamping connection, or the like. It is also conceivable that the coil element 70 is pressed into the assembly bushing 46 and a radially outward segment thereof bears on a radially inward segment of the assembly bushing 46 by means of a friction fit connection. It is further conceivable that the coil element 70 is retained by means of the end cap 54.

The drive device comprises a magnetic core 76 disposed in parallel to the coil element 70 and displaceably guided. When current is applied to the coil element 70, a magnetic field arises therein, so that the magnetic core 76 is displaced to the left or the right with reference to FIG. 1, depending on the polarity and current. In the embodiment shown in FIG. 1, the coil element 70 comprises a first coil L1 and a second coil L2 disposed coaxially adjacent to each other, and supplied with current alternatingly, as is described in more detail with reference to FIGS. 8A, 8B.

The magnetic core 76 is preferably implemented as a permanent magnet. The magnetic core 76 is fixedly connected to the membrane 42, preferably directly. For this purpose, the magnetic core 76 in the present embodiment example comprises a central through hole 78 through which a screw 80 extends. The screw 80 is disposed so that the screw head 82 thereof is present within the chamber 10 and makes surface contact with the end wall segment 14. The magnetic core 76 is implemented without an internal thread. In other embodiments, the magnetic core 76 can also comprise an internal thread, however, in order to connect the screw 80 directly.

In the present embodiment (FIG. 1), however, a nut 84 is provided and simultaneously forms a guide element 85. To this end, the nut 84 has an axial length L. The nut 84 runs through a pass-through opening 86 in the washer 77 with little clearance, so that the nut 84 is guided in the pass-through opening 86. The length L is dimensioned such that only the nut 84 is in contact with the washer 77 at both extreme deflections of the membrane 42, that is, at the left and right extreme positions, and does not come out of said washer. To this end, the nut 84 is made of a plastic, preferably a plastic having low friction, such as PEEK, and has an internal thread.

The end cap 54 comprises a bulge 88 implemented such that an axial end face of the nut 84 does not make contact with the end cap 54, regardless of the axial deflection. Noise emission is thereby further prevented. There is no mechanical stop with which the nut or magnetic contact make direct contact. The deflection is limited to the left with reference to FIG. 1 solely by the membrane 42, and simultaneously by the magnetic field, and to the right with reference to FIG. 1 by the membrane 42 and the magnetic field as well. Clicking or other impact noises are thereby not produced.

It can particularly additionally be provided that the assembly bushing 46 is made of a sound-damping material or that a sound-damping material is disposed in an intermediate space between the assembly bushing 46 and the housing 20. It is also conceivable to provide such a sound-damping material outside of the housing 20.

A very compact construction thus results. In the radial direction, the assembly unit 8 is not much larger than the diameter of the chamber 10 and in the axial direction is not much longer than is absolutely necessary due to the stroke of the membrane 42 and the drive 24. The construction is particularly smaller overall than for conventional structures having a rotating drive. Further reduction of the size results from the fact that the magnetic core 72 is not disposed centered within the coil element 70 in the resting position, as shown in FIG. 1, but rather is offset slightly to the right. Only half of the magnetic core 76 is particularly inserted into the coil element 70. Controlling is thereby simplified overall.

The magnetic core 76 preferably has a mass in the range of 1 g to approximately 10 g and/or a magnetic flux density in the range of 0.38 T to 0.4 T. Neodymium magnets are preferable. The magnetic core 76 preferably has a diameter in a range from 5 mm to 15 mm, preferably 6 mm to 10 mm, particularly preferably approximately 8 mm, and an axial length in the range of 3 mm to 15 mm, preferably 6 mm to 10 mm, particularly preferably approximately 8 mm. The magnetic core preferably has a retaining force of 15 to 35 N, preferably 20 to 30 N, particularly preferably approximately 25 N. Said core preferably has an energy product of 300 to 400 KJ/m$^3$, preferably approximately 340 to 360 KJ/m$^3$.

It is further preferable that the coil element has a flux density in a range from 0.13 mT to 500 mT. Said density is a function of the length of the coil element and the number of windings. It has been found that approximately 500 to 2000 windings, particularly approximately 500 to approximately 1000 windings at an axial length of approximately 4 mm to 20 mm, particularly 6 mm to 15 mm, particularly 8 mm, result in a suitable coil element.

The membrane 42 is made of a flexible material, such as a silicone material, but can also be made of a flexible and elastic plastic. The membrane 42 applies a return force to the magnetic core 72 in order to bring the same to the rest position.

According to a second embodiment (FIG. 3), the through hole 40 is closed and in this respect a floor 90 is implemented in the second circumferential wall segment 18. Two completely separated chambers are thereby formed, namely the chamber 10 comprising the opening 12, and an inner chamber 92 having no access to the surrounding area. The chamber 92 is preferably filled with an incompressible fluid, preferably a fluid for transmitting the motion of the membrane 42 to the second circumferential wall segment 18. Hygiene can thereby be further improved, as no bodily fluids can make contact with the first circumferential wall segment 16, the end wall segment 14, or the screw head 82, for example.

Figure 2:
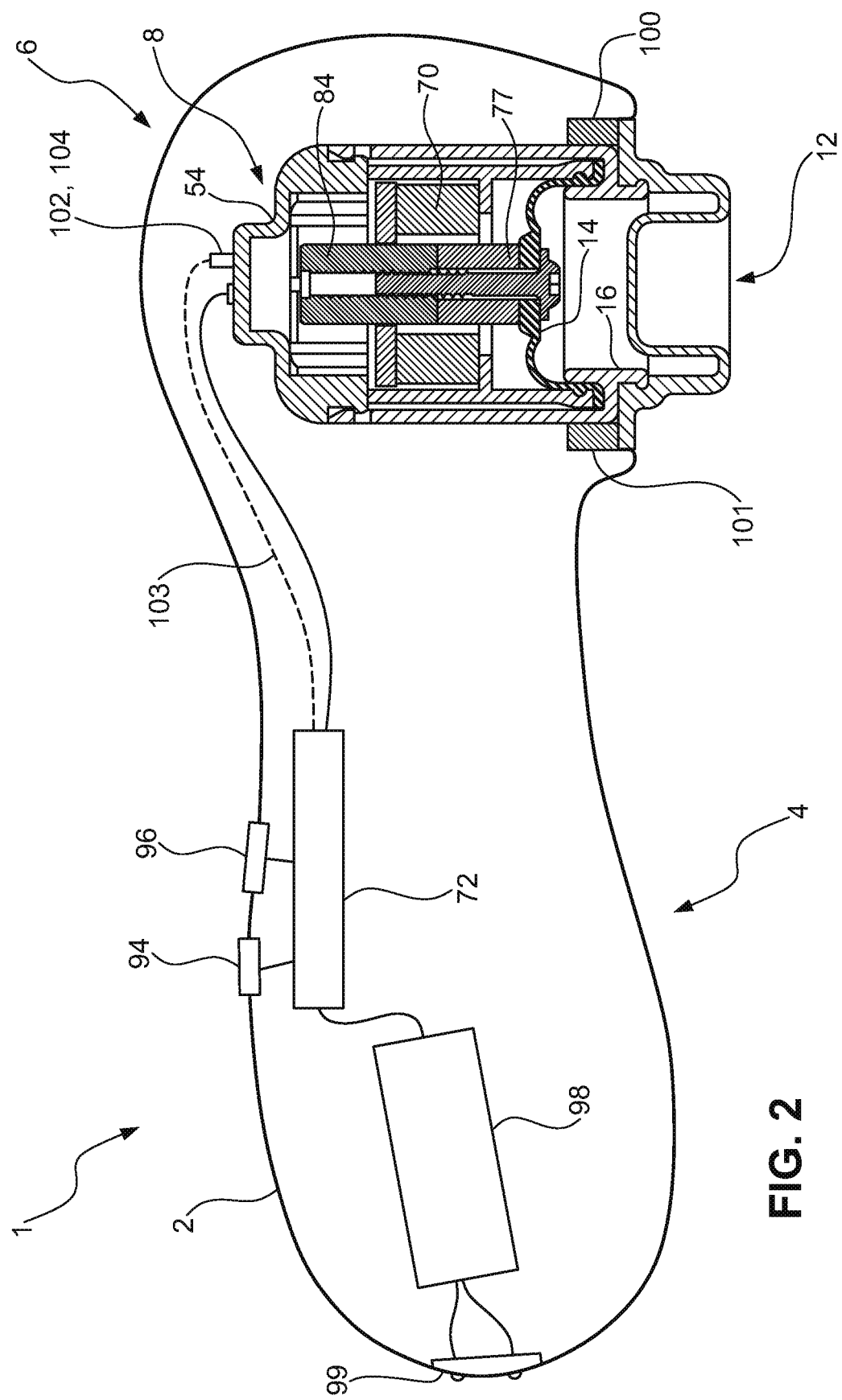
FIG. 2 is a full cross section through a massage device having the massage unit according to FIG. 1.

As can be seen in FIG. 2, the massage device 1 comprises an electronic control unit 72. The electronic control unit 72, for example implemented as a circuit board having corresponding electrical elements, is connected to a first and a second actuating knob 94, 96 by means of which the massage device 1 can be actuated. The control unit 72 is further connected to the coil element 70 in order to provide electrical current and corresponding signals to the same. The control unit 72 is also connected to a power source 98 implemented as a lithium-ion rechargeable battery and able to be recharged via a connection 99 by means of a corresponding plug. The connection 99 can be implemented particularly as described in DE 2009 008 634 U1, the disclosed content of which is fully incorporated herein by reference.

The actuating knob 94 is implemented as an actuating switch 94 and serves for switching on the massage device 1. The actuating knob 96 is implemented as a selector switch 96 for selecting a specified vibration profile or specified vibration stored in the control unit 50, according to which the coil element 70 is supplied with electrical current.

If the magnetic core 76 is displaced to the right with respect to FIG. 1 due to an induced magnetic field when the coil element is supplied with electrical current, then the membrane 42 is also displaced to the right as a result and the volume of the chamber 10 is reduced. Fluid present in the chamber 10 is compressed and/or caused to vibrate, whereby a pressure impulse arises and transits the chamber 10 as a wave and exits through the opening 12 and impinges on a body part of the user when positioned accordingly. A massage effect is thereby produced. If the magnetic core 76 is correspondingly displaced to the left, then the volume of the chamber 10 is increased again and an opposite impulse arises.

Figure 3:
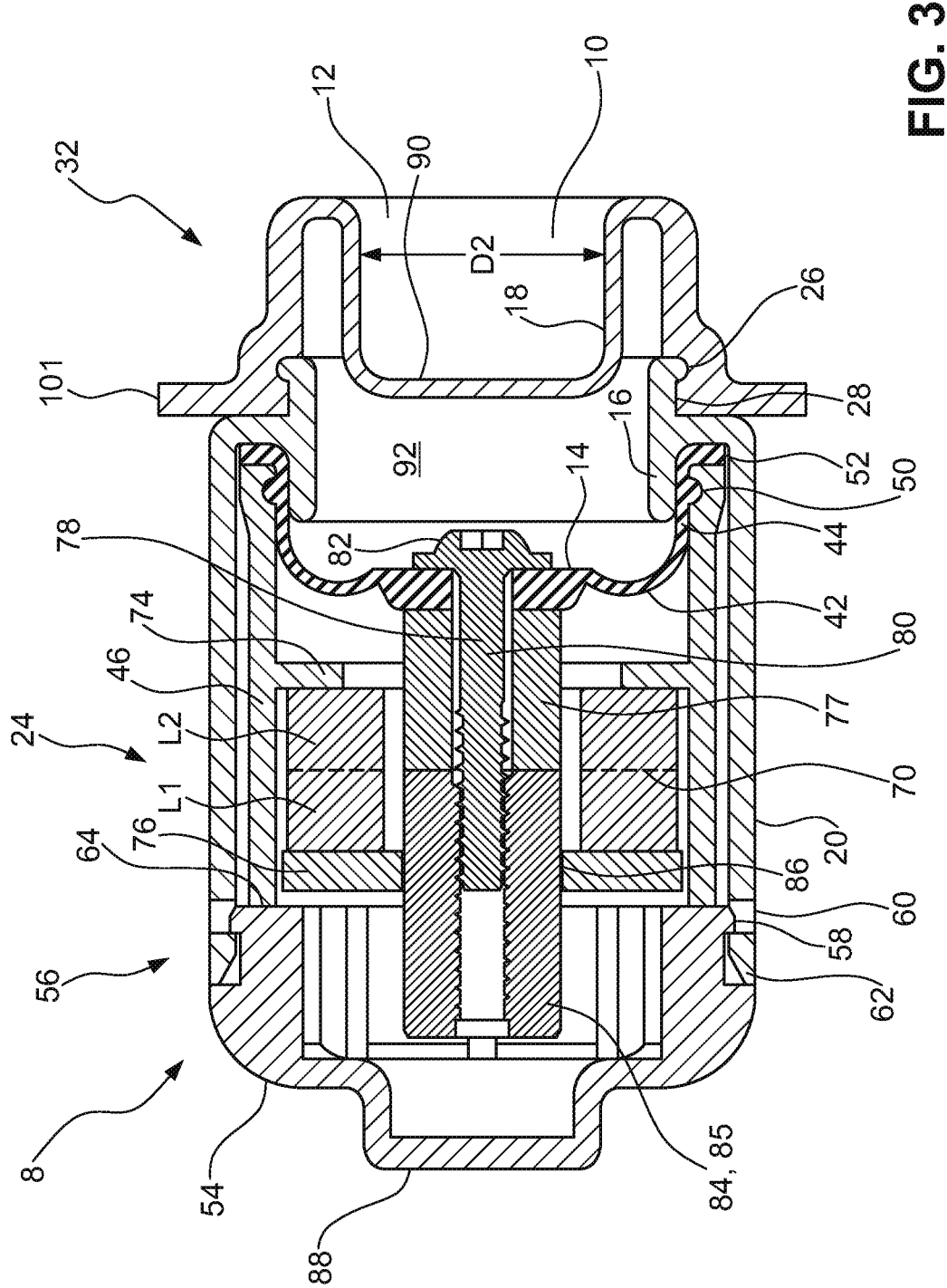
FIG. 3 is a second embodiment of a massage unit according the present disclosure.
Figure 4:
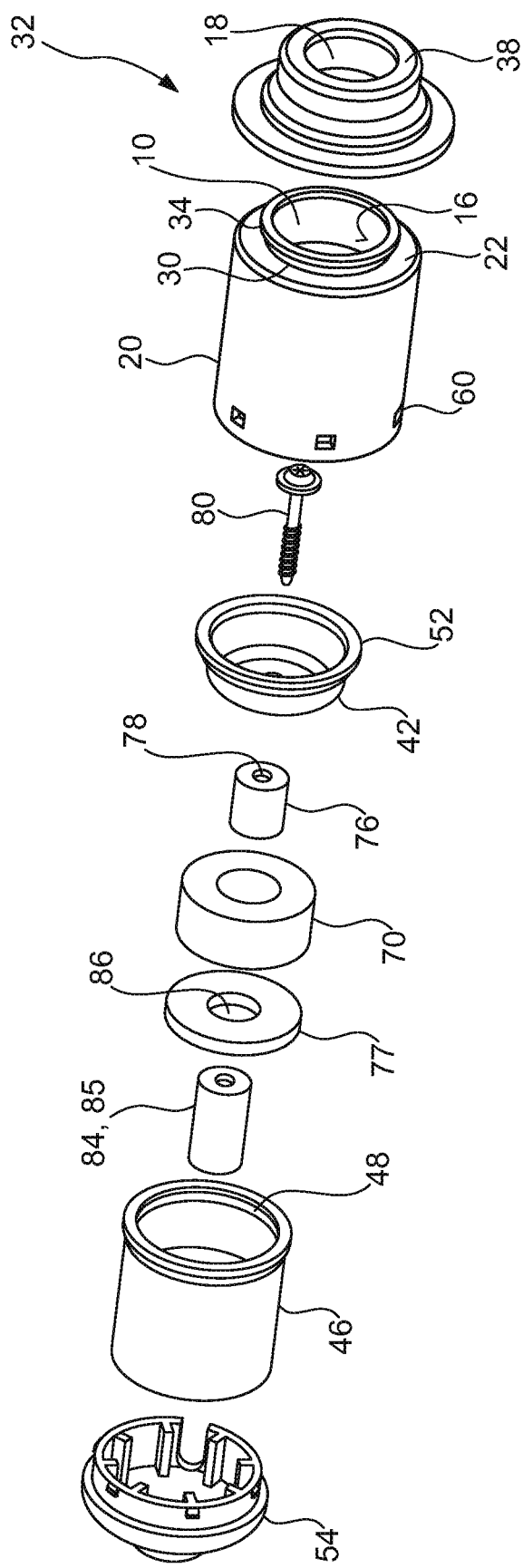
FIG. 4 is an exploded view of the massage unit according to FIG. 1.

It is further evident from FIG. 2 that an axially open annular groove 100 is provided in the housing 2, into which an axial protrusion 101 of the second circumferential wall segment 18, particularly the cap 32, can be inserted. While the axial segment in FIGS. 1 and 3 is shown as extending radially, it should be understood that said segment can also run in the axial direction. Particularly good sealing is thereby achieved, and furthermore the fit of the cap 32 is improved, so that said cap does not come loose on its own during operation. Nevertheless, the cap 32 can be removed without tools in a simple manner in order to clean the massage device 1 and particularly the chamber 10 as well.

Figure 5:
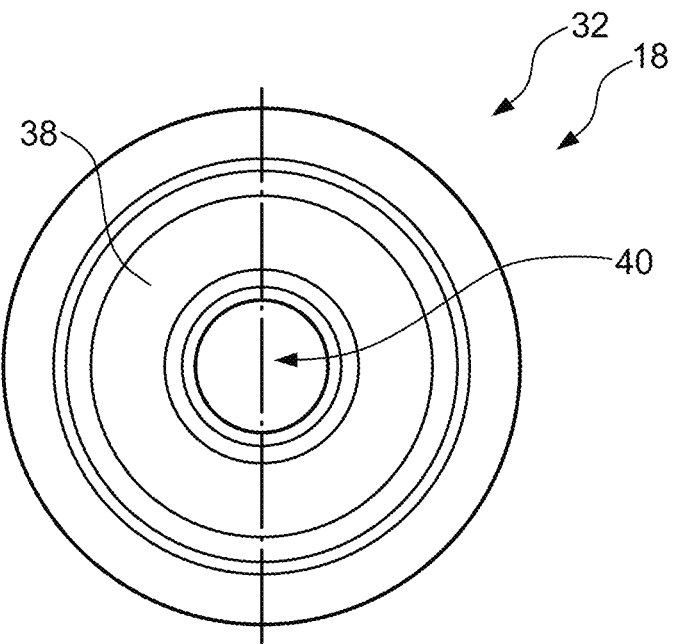
FIG. 5 is a front view of a cap forming a second circumferential wall segment according to the first embodiment example.
Figure 6:
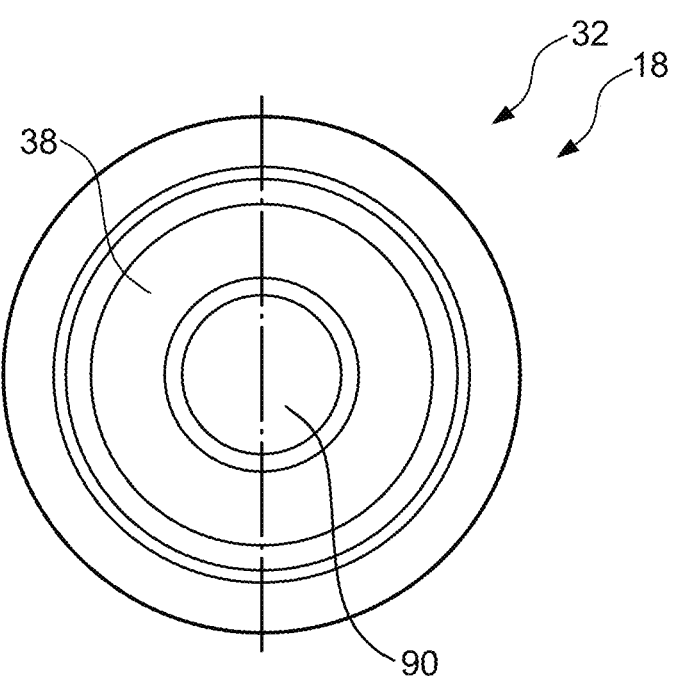
FIG. 6 is a front view of a cap forming the second circumferential wall segment according to a second embodiment example.

FIGS. 5 and 6 again show plan views of the second circumferential wall segment 18 and the cap 32. The cap 32 is shown in FIG. 5 as used in the first embodiment example (FIG. 1), and in FIG. 6 a cap 32 is shown as used in the second embodiment example (FIG. 3). The aperture 40 is provided for the cap 32 according to the first embodiment example (FIG. 1, 5), while the cap 32 according to the second embodiment example (FIGS. 3 and 6) comprises the floor 90.

It can also be provided that the massage device 1 is provided having both variants of caps 32, so that a user can change out the caps 32 as desired.

Figure 7A:
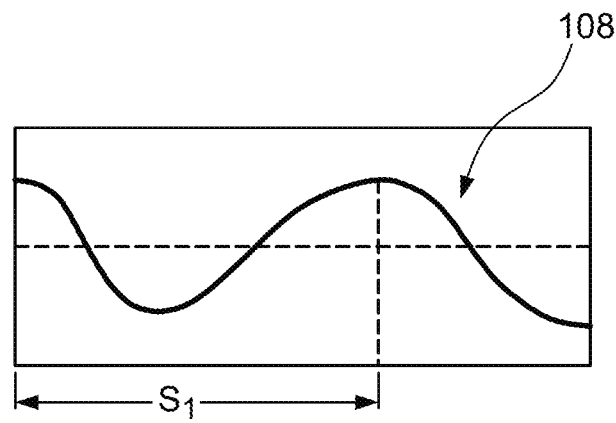
FIGS. 7A-7C are vibration profiles for exciting a coil element of embodiments according to the present disclosure.
Figure 7B:
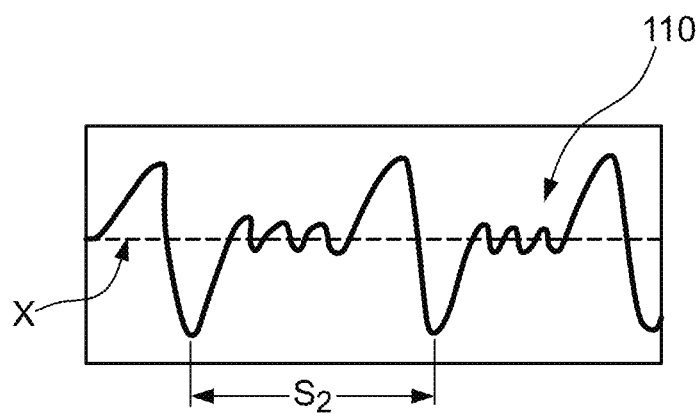
Figure 7C:
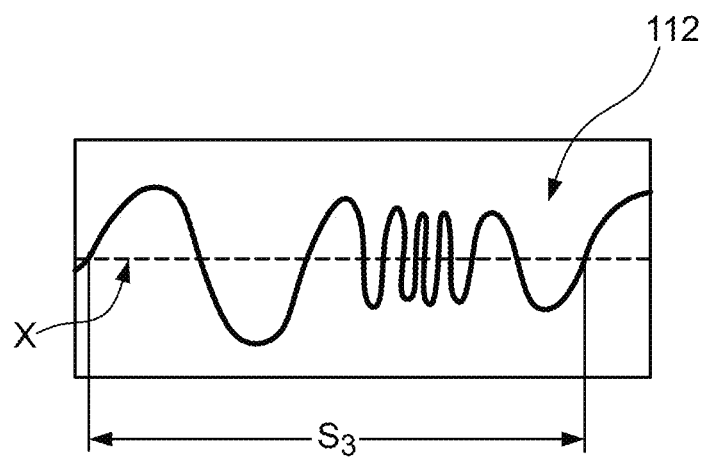

Three vibration profiles 108, 110, 112 are shown in the subsequent FIG. 7A through 7C and can be used for exciting the coil element 76. The vibration profiles represent a motion of the magnetic core 76, wherein the origin line X illustrates a resting position, as shown in FIGS. 1 and 3, of the magnetic core 76 and the amplitude toward the top with respect to FIG. 7A through 7C represents a motion of the magnetic core 76 to the right. The amplitude below the X line in FIG. 7A through 7C correspondingly represents a motion of the magnetic core 76 to the left with respect to FIGS. 1 and 3.

FIG. 7A shows a uniform, sinusoidal excitation using a vibration profile 108, wherein the membrane 42 oscillates sinusoidally and thus a sinusoidal vibration is also induced in the chamber 10.

FIG. 7B shows a vibration profile 110 made of three short vibrations having a small amplitude and a somewhat longer vibration having a higher amplitude. A pulsating situation perceived as particularly arousing is thereby achieved. The variable amplitude can be achieved by the special nature of the drive device 24 having the coil element 70 and the magnetic core 76. Said nature of the drive device 24 allows various amplitudes to be used.

FIG. 7C finally shows a vibration profile 112 having a uniform amplitude, wherein the frequency varies. The vibration profile begins at a relatively slow frequency, is then increased, and finally becomes slower again. A wave-shaped frequency increase is thus provided, and a wave-shaped pulsating pressure profile is provided accordingly in the chamber 10 and the opening 12.

A working point of the massage device 1 according to the present disclosure lies within a range from >0 Hz to 200 Hz and preferably in a range of approximately 100 Hz. It has been found that frequencies in a range of 200 Hz can be achieved by means of the drive device 24 as described here, but that the massage effect is thereby lower, as vibrations above 200 Hz are difficult for the human body to perceive. Vibrations in the range of 100 Hz are particularly suitable, as said vibrations produce a particularly pleasant massage.

It is evident from FIG. 2 that a Hall-effect sensor 102 is provided for measuring the magnetic flux density of the magnetic core 76. The Hall-effect sensor 102 can thus measure the position of the magnetic core 76 relative to the Hall-effect sensor 102 and thus relative to the coil element 70. The Hall-effect sensor can thereby indirectly determine the position of the end wall segment 14. The Hall-effect sensor 102 is connected to the control unit 72 by means of an electrical line and provides corresponding signals to the same. The control unit 72 is set up for adapting or selecting the vibration profile 108, 110, 112 accordingly, based on the signal received by the Hall-effect sensor 102, in order to achieve an effective massage. Complete closed-loop control is thereby achieved. Alternatively to the Hall-effect sensor 102, it is also possible to use an optical sensor 104 for optically measuring the distance between the cap 54 and the nut 84. It is also possible, of course, to use a different point, such as directly measuring a distance between the membrane 42 and the protrusion 74 or the like.

In order to obtain vibration profiles as in FIGS. 7A through 7C, the coil element must be actuated accordingly. Two impulse diagrams depicting the actuating of the coil element 70 are shown in FIGS. 8A and 8B.

The top two graphs (FIG. 8A) show the actuating of a coil element 70 having a first coil L1 and a second coil L2, and the bottom graph (FIG. 8B) shows the actuating of a coil element 70 comprising only one single coil L. For the case of two coils L1, L2 it is sufficient to actuate each of the coils L1, L2 by means of a current without thereby changing polarity. If only one coil L is used, then it is necessary to reverse the polarity in order to effectively displace the magnetic core in opposite directions. The magnetic core could alternatively be drawn into a position by means of a spring, or due to the magnetic force thereof, but then the acceleration depends on said pretension and the options for defining vibration profiles are limited.

The two diagrams show the current provided to each coil L1, L2, L. For the two coils L1, L2 (FIG. 8A), only the states "1" and "0" are shown, and for the single coil L (FIG. 8B), three states "+", "0", and "−" are shown in order to show the bipolar actuation.

The graphs show one potential variants, and it should be understood that a plurality of variants are possible depending on requirements.

For the embodiment having two coils L1, L2 (FIG. 8A), the first coil L1 is first energized for 30 ms. The magnetic core is accelerated in a first direction (e.g., to the left with respect to FIG. 1). After 30 ms, the energizing is stopped and the magnetic field dissipates. The magnetic core can return to the resting position thereof. A 60 ms waiting time occurs. The second coil L2 is then energized and the magnetic core is accelerated in the other direction (to the right with respect to FIG. 1, for example). Now a further 240 ms waiting time occurs in the embodiment example shown, until the first coil L2 is energized in turn. The duration of energizing and the pauses can be selected freely and are particularly dependent on the dynamics and inertia of the entire system.

The control unit 72 is preferably set up for modifying the duration of energizing and pausing based on the signals of the Hall-effect sensor 102 in order to achieve a selected vibration profile (FIG. 7A through 7C).

The second graph (FIG. 8B) shows the same excitation of the magnetic core but implemented by means of only one coil L. The coil L is first actuated for 30 ms at a first polarity, then a pause of 60 ms follows, and then the coil L is energized at the reverse polarity for 30 ms. The pose of 240 ms then follows.

Particularly effective vibration profiles are obtained if the actuating is asymmetrical, for example if irregular pause durations are used. It is shown at the right side of FIGS. 8A and 8B, for example, that only one pause of 10 ms is provided.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A massage device, comprising: a housing having a handle segment and a massage segment; at least one chamber having an opening leading outward in the massage segment, the at least one chamber including an end wall segment, disposed opposite the opening, and a first circumferential wall segment, the first circumferential wall segment defining the opening, wherein the end wall segment is at least partially displaceable, wherein the first circumferential wall segment is substantially flexible; a drive device configured to induce a predetermined vibration in the end wall segment, wherein the drive device includes at least one coil element and at least one magnetic core, the at least one magnetic core displaceably guided and disposed parallel to the coil element and connected to the end wall segment, the drive device further including a guide element for guiding the magnetic core relative to the coil element, wherein the guide element is a sleeve; and a fastener extending through a center of the end wall segment, the sleeve structured to be disposed on the fastener.

2. The massage device according to claim 1, further comprising a second circumferential wall segment being disposed between the end wall segment and the first circumferential wall segment, wherein the second circumferential wall segment is substantially rigid.

3. The massage device according to claim 2, wherein the first circumferential wall segment and the second circumferential wall segment have approximately the same diameter.

4. The massage device according to claim 2, wherein the second circumferential wall segment is a hard plastic material with a coating on an interior surface of the second circumferential wall segment.

5. The massage device according to claim 2, wherein the first circumferential wall segment is connected to the second circumferential wall segment by two-component injection molding.

6. The massage device according to claim 2, wherein the first circumferential wall segment includes a removable cap connected to the second circumferential wall segment with a clamping connection.

7. The massage device according to claim 6, wherein the second circumferential wall segment includes an annular bulge around a radially outwardly open circumferential groove, and the first circumferential wall segment includes a corresponding radial protrusion structured to be received in the circumferential groove to attach the first circumferential wall segment to the second circumferential wall segment.

8. The massage device according to claim 6, wherein one of the second circumferential wall segment and the housing includes an axially open annular groove, and the first circumferential wall segment includes a corresponding axial protrusion structured to be received in the annular groove.

9. The massage device according to claim 1, wherein the at least one chamber has a substantially cylindrical or conical shape tapering down in a direction of the end wall segment.

10. The massage device according to claim 1, wherein the first circumferential segment is a silicone material.

11. The massage device according to claim 10, wherein the silicone material is a medical silicone material having a Shore hardness in a range from Shore 5 to Shore 50.

12. The massage device according to claim 1, wherein the first circumferential wall segment has a wall thickness in a range from 0.5 mm to 5 mm.

13. The massage device according to claim 1, wherein the first circumferential wall segment is structured to be reversibly and non-destructively removable and replaceable.

14. The massage device according to claim 1, wherein the first circumferential wall segment includes an inner collar extending radially and integrally formed on the first circumferential wall segment spaced apart from the opening.

15. The massage device according to claim 1, wherein the magnetic core is fixedly and directly connected to the end wall segment.

16. The massage device according to claim 1, wherein the magnetic core is connected to the end wall segment with the fastener.

17. The massage device according to claim 1, further comprising:
a control unit including a circuit board and a plurality of electric elements, the control unit configured to control the drive device and a measuring device for determining a location of the magnetic core relative to the coil element and, the measuring device configured to provide a determined location of the magnetic core to the control unit, wherein the control unit is configured to control the drive unit as a function of the determined location of the magnetic core.

18. The massage device according to claim 17, wherein the measuring device includes at least one of an optical sensor and a Hall-effect sensor.

19. The massage device according to claim 1, wherein a noise emission when the drive device is activated is less than 40 dBA, measured at a room temperature of 25° C. and ambient pressure from a distance of 30 cm from the opening, wherein the massage device is clamped at the handle segment and free at the massage segment.

20. The massage device according to claim 19, wherein 80% or more of the noise emission is in a frequency range from 40 to 200 Hz.

21. The massage device according to claim 19, wherein 80% or more of the noise emission is pink noise or red noise.

22. The massage device according to claim 1, wherein the predetermined vibration is a non-sinusoidal vibration.

23. The massage device according to claim 22, wherein the predetermined vibration is a sawtooth vibration, a rectangular vibration, a triangular vibration, or a mixture thereof.

24. The massage device according to claim 22, wherein the predetermined vibration has a variable amplitude.

25. The massage device according to claim 1, wherein the fastener extends through a central through hole in the magnetic core.

* * * * *